United States Patent
Williams

(10) Patent No.: US 11,033,307 B2
(45) Date of Patent: *Jun. 15, 2021

(54) ALIGNMENT GUIDE FOR CERVICAL SPINE PLATE

(71) Applicant: Seth K. Williams, Madison, WI (US)

(72) Inventor: Seth K. Williams, Madison, WI (US)

(73) Assignee: Seth K. Williams, Madison, WI (US)

( * ) Notice: Subject to any disclaimer, the term of this patent is extended or adjusted under 35 U.S.C. 154(b) by 9 days.

This patent is subject to a terminal disclaimer.

(21) Appl. No.: 16/423,514

(22) Filed: May 28, 2019

(65) Prior Publication Data

US 2019/0274744 A1 Sep. 12, 2019

Related U.S. Application Data

(63) Continuation of application No. 15/820,036, filed on Nov. 21, 2017, now Pat. No. 10,314,627, which is a
(Continued)

(51) Int. Cl.
| | | |
|---|---|---|
| *A61B 17/80* | (2006.01) | |
| *A61B 17/70* | (2006.01) | |
| *A61B 17/02* | (2006.01) | |
| *A61B 17/56* | (2006.01) | |
| *A61B 17/68* | (2006.01) | |

(52) U.S. Cl.
CPC ........ *A61B 17/808* (2013.01); *A61B 17/7044* (2013.01); *A61B 17/7058* (2013.01); *A61B 17/7059* (2013.01); *A61B 2017/0256* (2013.01); *A61B 2017/567* (2013.01); *A61B 2017/681* (2013.01)

(58) Field of Classification Search
CPC ............ A61B 17/7005; A61B 17/7007; A61B 17/7044; A61B 17/7049; A61B 17/1728; A61B 17/808; A61B 17/663; A61B 2017/681; A61B 17/7074; A61B 7/7083; A61B 17/7091; A61B 17/7082; A61B 17/8894; A61B 17/666
See application file for complete search history.

(56) References Cited

U.S. PATENT DOCUMENTS 4,978,348 A * 12/1990 Ilizarov .............. A61B 17/6425
606/105
6,007,535 A * 12/1999 Rayhack ................ A61B 17/15
606/105
(Continued)

*Primary Examiner* — Anu Ramana
(74) *Attorney, Agent, or Firm* — Bell & Manning, LLC; Christopher Kalafut

(57) ABSTRACT

A cervical spine plate attachment system includes a cervical spine plate that has a first surface configured to rest upon a first vertebra and a second vertebra, a second surface opposite the first surface and facing away from the first vertebra and the second vertebra, and a plurality of holes configured to receive fasteners to secure the cervical spine plate to the first vertebra and the second vertebra. The system also includes an alignment guide that detachably mounts to the cervical spine plate. The alignment guide comprises a pair of bars that rest upon the second surface of the cervical spine plate when the alignment guide is mounted to the cervical spine plate. The system also includes a fastener configured to secure the alignment guide to the cervical spine plate.

18 Claims, 11 Drawing Sheets

Related U.S. Application Data continuation of application No. 15/255,598, filed on Sep. 2, 2016, now Pat. No. 9,839,457, which is a continuation of application No. 15/200,447, filed on Jul. 1, 2016, now Pat. No. 9,962,206.

(60) Provisional application No. 62/260,868, filed on Nov. 30, 2015.

(56) References Cited

U.S. PATENT DOCUMENTS

| | | | | |
|---|---|---|---|---|
| 6,066,142 | A * | 5/2000 | Serbousek | A61B 17/1728 |
| | | | | 606/70 |
| 7,291,152 | B2 * | 11/2007 | Abdou | A61B 17/7059 |
| | | | | 606/279 |
| 8,986,357 | B2 * | 3/2015 | Jensen | A61B 17/7074 |
| | | | | 606/326 |
| 9,101,422 | B2 * | 8/2015 | Freid | A61B 17/8047 |
| 2004/0019353 | A1 * | 1/2004 | Freid | A61B 17/808 |
| | | | | 606/915 |
| 2006/0200134 | A1 * | 9/2006 | Freid | A61B 90/92 |
| | | | | 606/71 |
| 2012/0078304 | A1 * | 3/2012 | Jensen | A61B 17/7071 |
| | | | | 606/251 |
| 2013/0304067 | A1 * | 11/2013 | Hess | A61B 17/8004 |
| | | | | 606/71 |

* cited by examiner

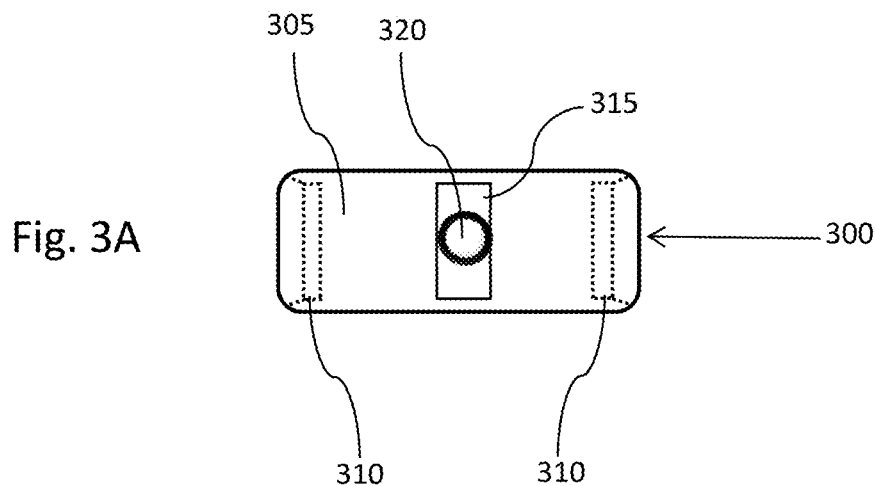
Fig. 3A
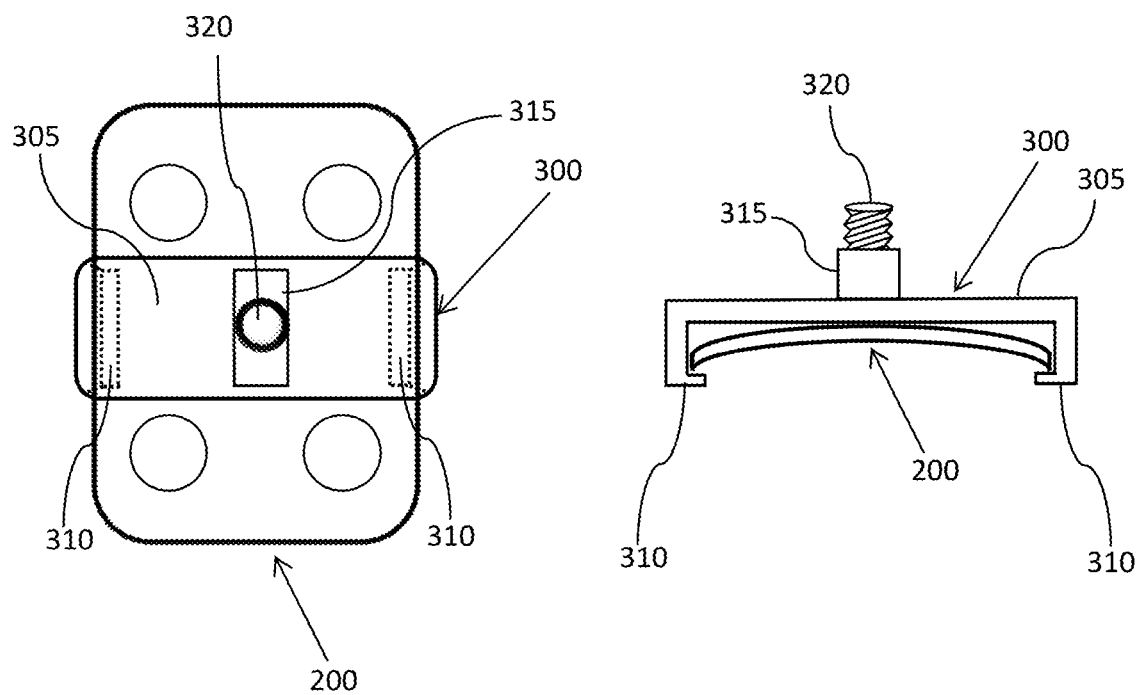
Fig. 3B
Fig. 3C

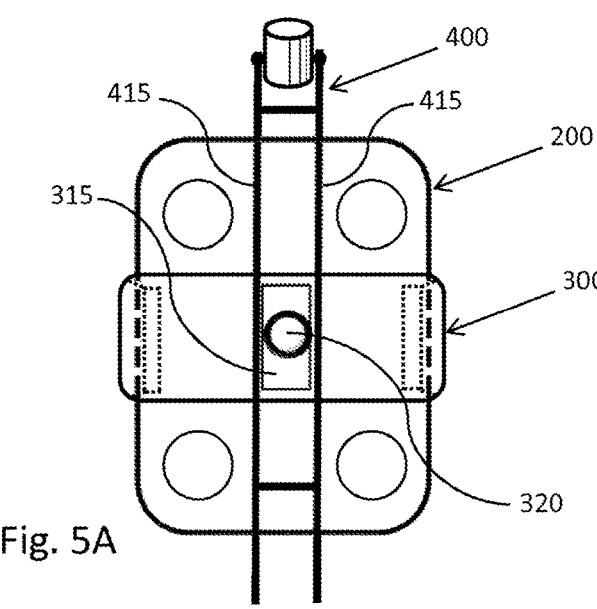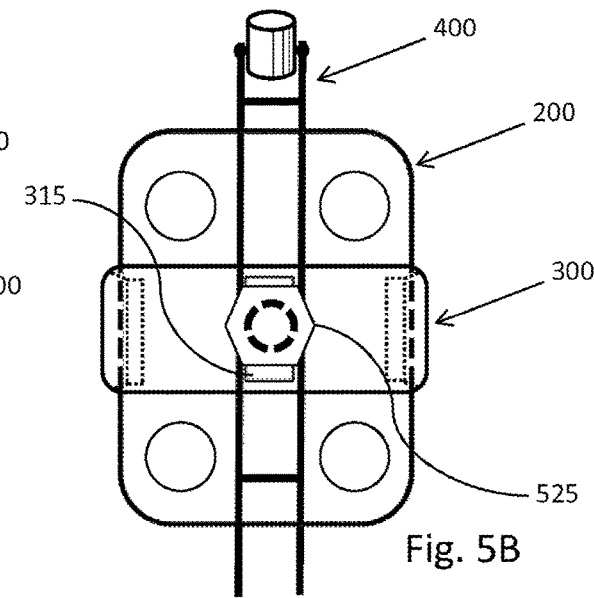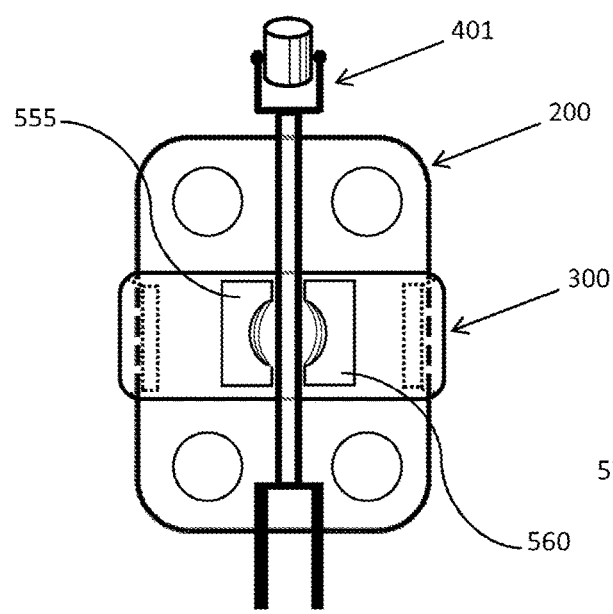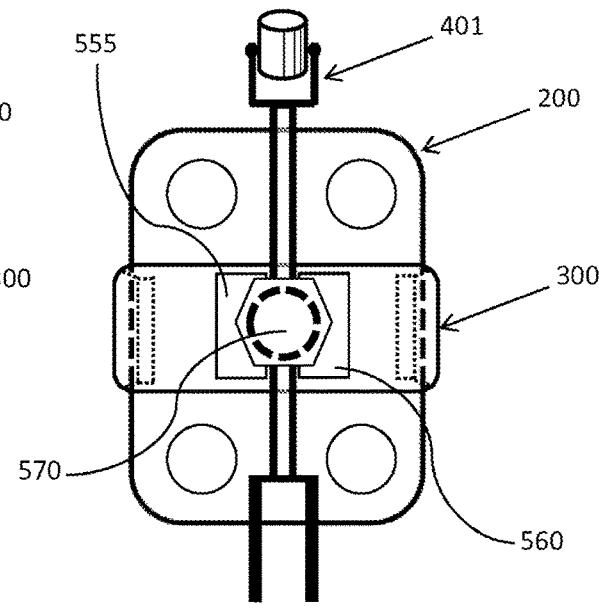

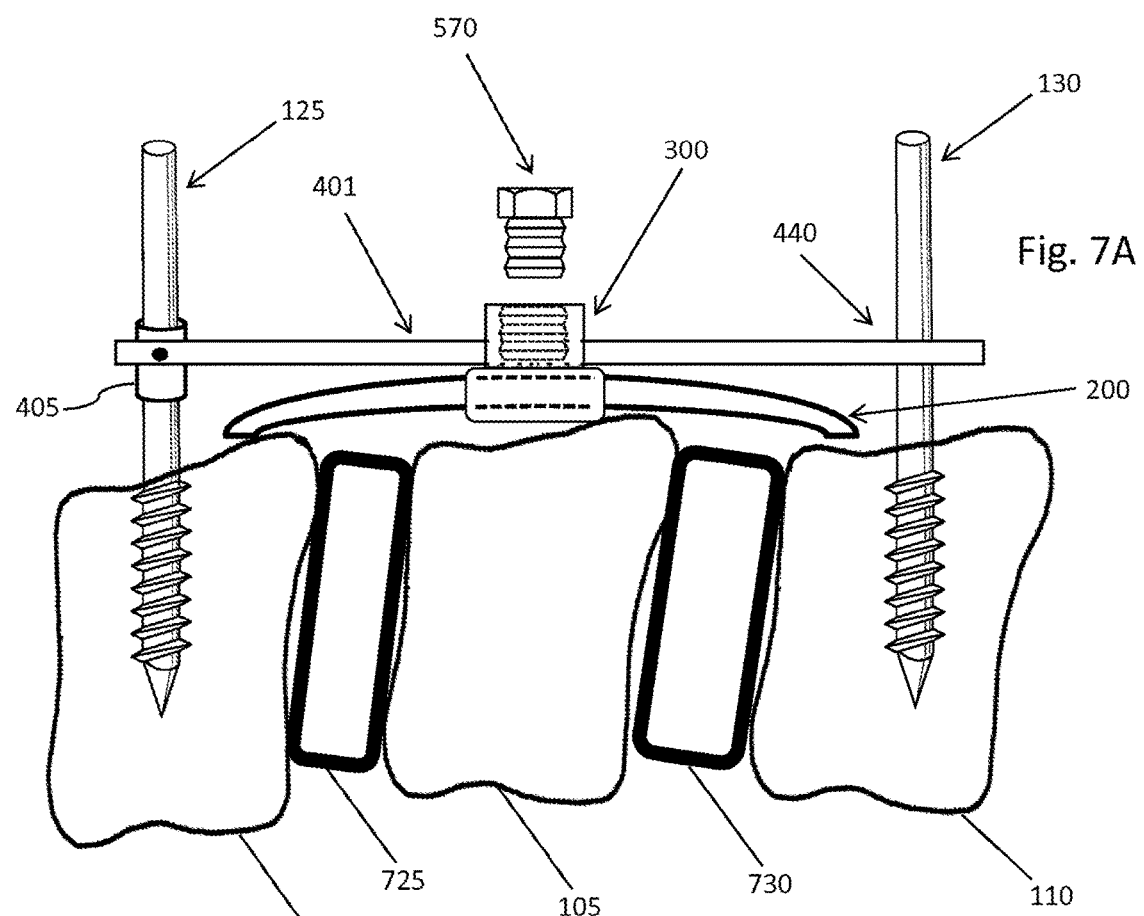
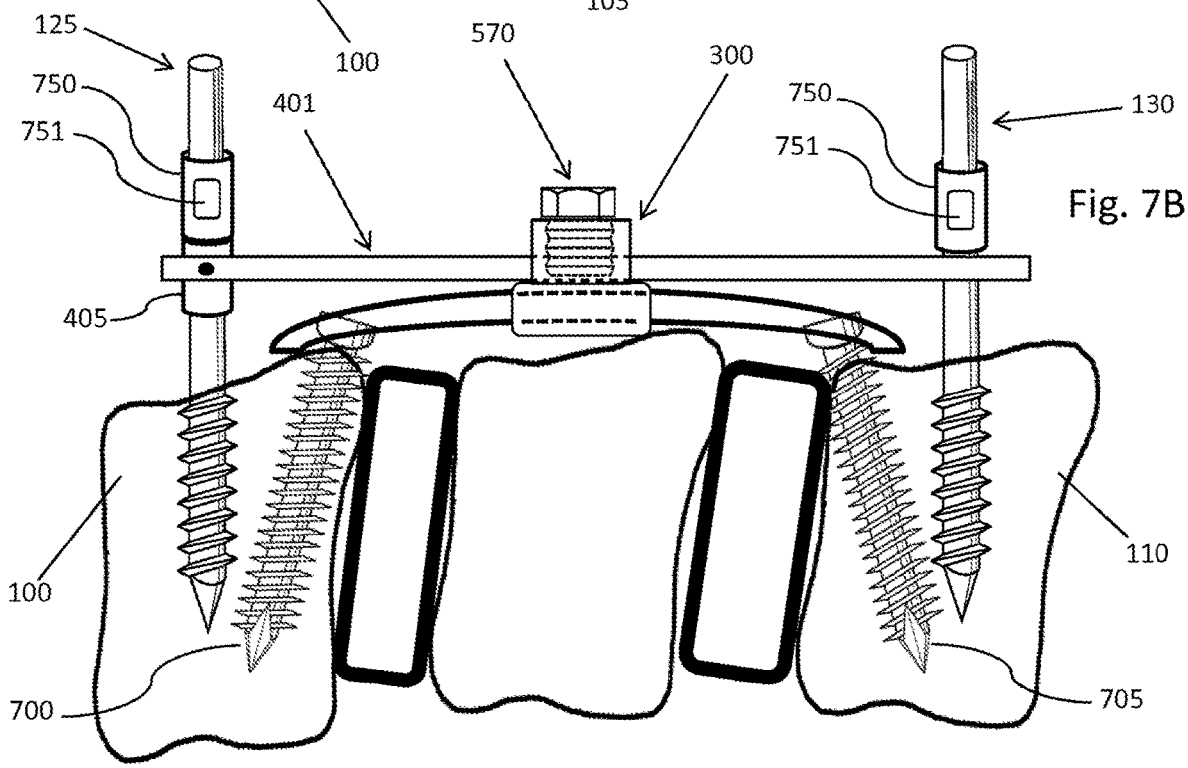

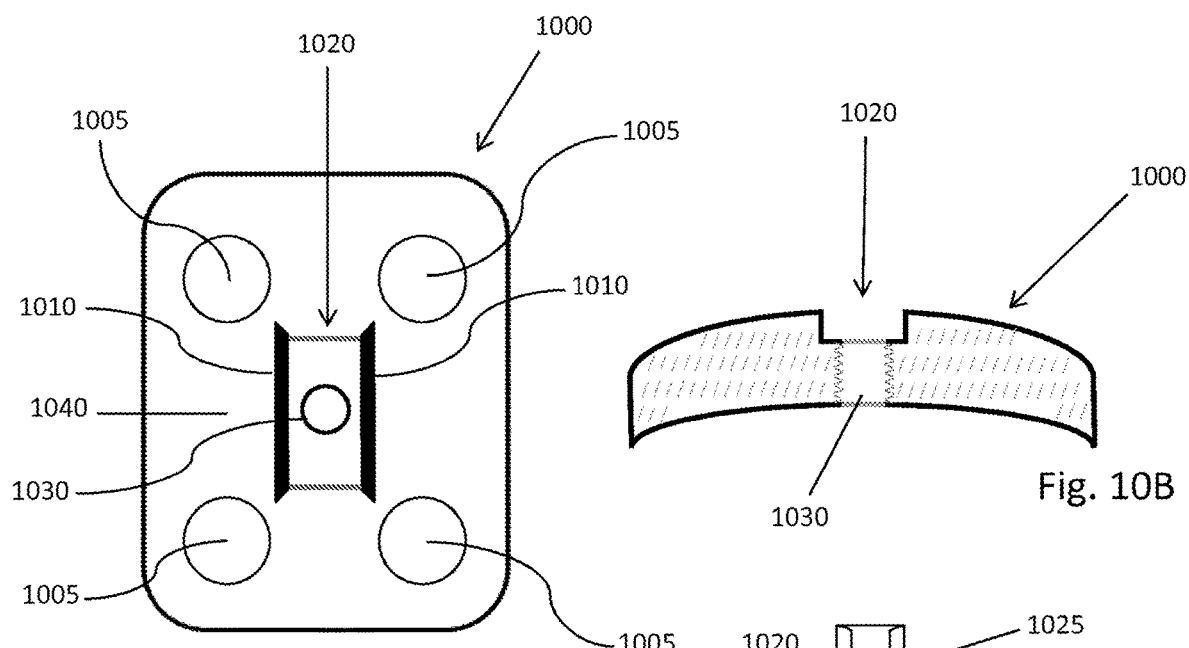
Fig. 10A
Fig. 10B
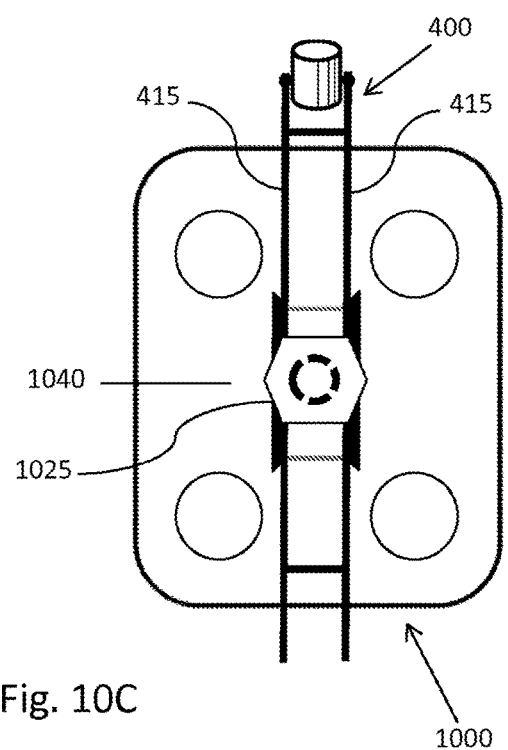
Fig. 10C
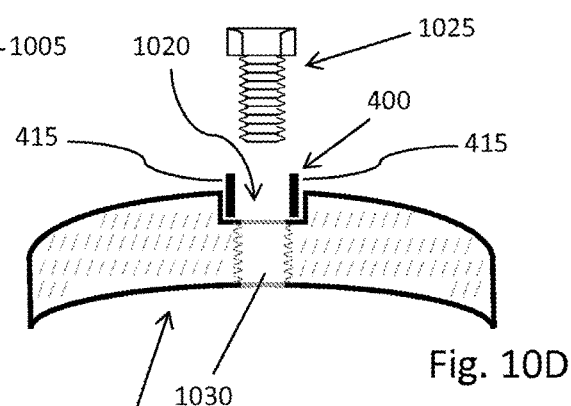
Fig. 10D
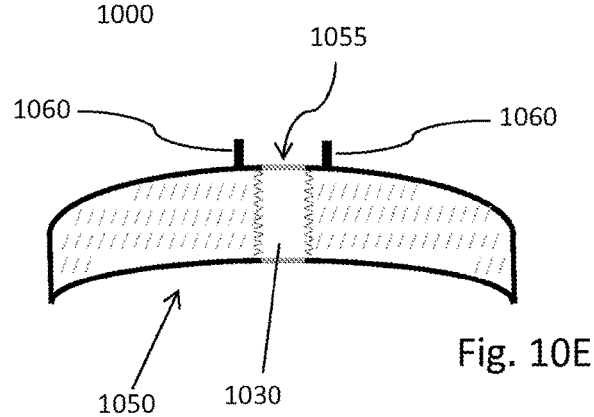
Fig. 10E

ALIGNMENT GUIDE FOR CERVICAL SPINE PLATE

CROSS-REFERENCE TO RELATED APPLICATIONS

The present application is a Continuation of U.S. patent application Ser. No. 15/820,036 filed on Nov. 21, 2017, which is a Continuation of U.S. patent application Ser. No. 15/255,598 filed on Sep. 2, 2016, which is a Continuation of U.S. patent application Ser. No. 15/200,447 filed on Jul. 1, 2016, which claims the priority benefit of U.S. Provisional Patent Application No. 62/260,868 filed on Nov. 30, 2015, the entire disclosures of which are hereby incorporated by reference herein.

BACKGROUND

Cervical spine plates are commonly used in anterior cervical spine fusion operations to stabilize the spine while the fusion heals. The typical surgical sequence is to perform an anterior cervical discectomy, followed by placement of a structural bone graft or cage with bone graft into the disk space for the fusion. This is followed by placement of an anterior cervical plate, and screws are used to attach the plate to the vertebral bodies above and below the disk space into which the graft/cage was placed.

SUMMARY

A cervical spine plate attachment system includes a bracket and an alignment guide. The bracket is configured to mount to a cervical spine plate. The alignment guide includes a first connector proximate to a first end of the alignment guide, wherein the first connector is configured to attach to a first pin inserted into a first vertebra. The alignment guide also includes a second connector proximate to a second end of the alignment guide, wherein the second connector is configured to attach to a second pin inserted into a second vertebra. The alignment guide further includes a fastener configured to secure the alignment guide to the bracket such that the alignment guide is secured to the cervical spine plate. A cervical spine plate can also be designed to attach directly to an alignment guide without the use of a bracket.

A method for mounting a cervical spine plate includes mounting the cervical spine plate to an alignment guide. The method also includes placing the alignment guide over distraction pins which are mounted to vertebrae. The method also includes drilling holes into the vertebrae such that the cervical spine plate can be secured to the vertebrae, wherein the drilling is performed using the secured cervical spine plate as a guide. The method further includes securing the cervical spine plate to the vertebrae with fasteners.

Another illustrative cervical spine plate attachment system includes a cervical spine plate that has a first surface configured to rest upon a first vertebra and a second vertebra, a second surface opposite the first surface and facing away from the first vertebra and the second vertebra, and a plurality of holes configured to receive fasteners to secure the cervical spine plate to the first vertebra and the second vertebra. The system also includes an alignment guide that detachably mounts to the cervical spine plate. The alignment guide comprises a pair of bars that rest upon the second surface of the cervical spine plate when the alignment guide is mounted to the cervical spine plate. The system also includes a fastener configured to secure the alignment guide to the cervical spine plate.

Another illustrative method for mounting a cervical spine plate includes mounting an alignment guide to a cervical spine plate that includes a first surface configured to rest upon a first vertebra and a second vertebra and a second surface opposite the first surface. The alignment guide is mounted such that at least a portion of the alignment guide rests upon the second surface of the cervical spine plate. The method also includes attaching a first connector of the alignment guide to a first distraction pin that is mounted to a first vertebra. The method also includes attaching a second connector of the alignment guide to a second distraction pin that is mounted to a second vertebra. The method also includes drilling holes into the first vertebra and the second vertebra while using openings in the cervical spine plate as a guide. The method further includes securing the cervical spine plate to the first vertebra and the second vertebra by placing fasteners through the openings in the cervical spine plate and into the drilled holes.

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

BRIEF DESCRIPTION OF THE DRAWINGS

FIG. 3A is a front view, or an anterior view, of a bracket that attaches to a cervical spine plate and an alignment guide in accordance with an illustrative embodiment.

FIG. 3B is a front view of a bracket attached to a cervical spine plate in accordance with an illustrative embodiment.

FIG. 3C is a side view of a bracket attached to a cervical spine plate in accordance with an illustrative embodiment.

FIGS. 5A, 5B, 5C, and 5D are front views, or anterior views, of the cervical spine plate secured to the cervical spine plate alignment guide via a bracket, in accordance with illustrative embodiments.

FIG. 7A is a side view of a cervical spine with interbody fusion cages between the vertebral bodies, with a cervical spine plate attached to the vertebral body on the left and the vertebral body on the right with screws, in accordance with an illustrative embodiment. Distraction pins are depicted in the vertebral bodies, and the cervical spine plate alignment guide is mounted on the distraction pins. The bracket is attached to the cervical spine plate and is being attached to the cervical spine plate alignment guide with a bolt, in accordance with an illustrative embodiment.

FIG. 7B shows the same configuration as FIG. 7A, with the addition of clamps that secure the cervical spine plate alignment guide to the distraction pins, in accordance with an illustrative embodiment.

FIGS. 10A through 10E are front or anterior views (FIGS. 10A and 10C) and cross-sectional views (FIGS. 10B, D, and E) of an anterior cervical spine plate with a groove or channel and screw hole designed to directly mate to an alignment guide without using a bracket, in accordance with illustrative embodiments.

DETAILED DESCRIPTION

Figure 1:
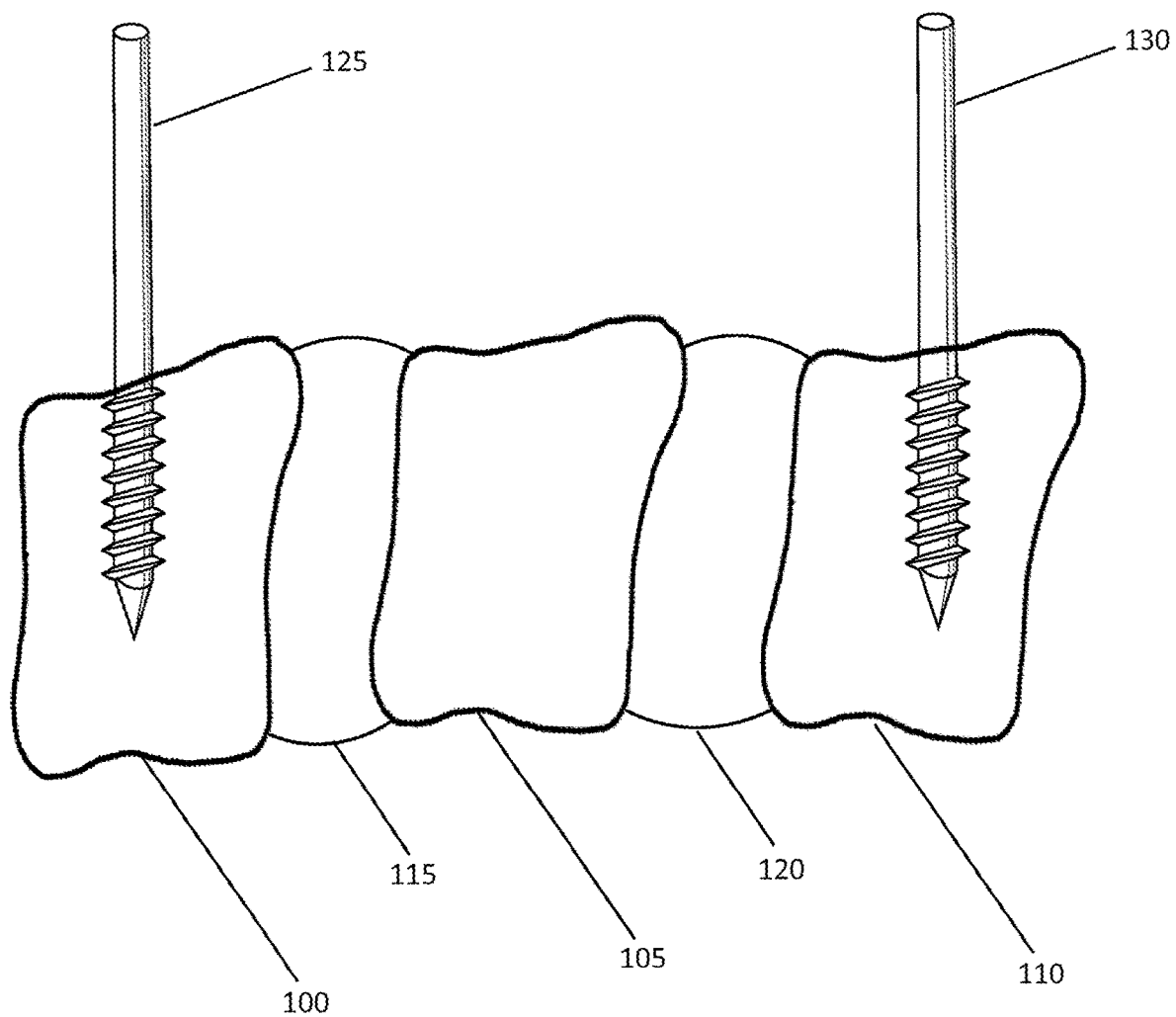
FIG. 1 is a side view of distraction pins attached to vertebrae in accordance with an illustrative embodiment.

A cervical spinal fusion can be performed at a single level (i.e., across a single disc) or multiple levels (i.e., across multiple discs), with a single cervical spine plate spanning the one level or multiple levels. Ideally the cervical spine plate is placed in the exact midline of the cervical spine when viewed from the front (i.e., anterior view), but this can be difficult and often the plate ends up being placed to the left or right of midline during surgery. Spine surgeons often lament the difficulty in placing the anterior cervical spine plate in the desired position. For example, a common method of applying the anterior cervical spine plate is by provisionally securing the plate to the vertebral body by placing a small pin which may be threaded through the plate into the bone. However, due to the curvature of the anterior vertebral bodies and other factors, it can be difficult to precisely secure the plate in the desired position prior to drilling the screw holes and while placing the screws that secure the plate to the bone. The drill can drift slightly cephalad, caudal, left and/or right as the drilling is done, and the plate ends up then being placed in a suboptimal position.

As a result, a common problem that occurs during such surgeries is that the cervical spine plate is positioned slightly to one side or another at the upper level and further off to the left or right at the level or levels below, resulting in the plate being placed slightly oblique instead of straight when viewed from the front or on an anteroposterior (AP) X-ray. Even when the plate is applied straight, it can be easy to position it to the left or right of midline. Another common problem that occurs is placement of the plate higher (more cephalad) on the uppermost vertebral body in the fusion construct, which results in the plate being placed closer to the uninvolved cephalad disc than is ideal.

Described herein is a cervical spine plate alignment guide that allows a surgeon to easily place the plate in the midline of the cervical spine, straight when viewed from the front and on the anteroposterior (AP) X-ray view, while keeping the plate as low as possible on the uppermost vertebral body in the fusion construct. In order to facilitate an anterior cervical discectomy and fusion, distraction pins can be placed in the vertebral body above and below the fusion. As the disk is removed, distraction can be placed across the distraction pins, allowing for better access to the disk space to decompress the neural elements. The cervical spine plate alignment guide is based off of these distraction pins. The surgeon places the distraction pins precisely in the midline of the vertebral bodies above and below the fusion level. Once this is accomplished, the pins can later be used with the alignment guide to place the plate in the exact desired position. Specifically, the cervical spine plate alignment guide, which is secured to the distraction pins, functions to rigidly hold the plate in place so that the cervical spine plate can be placed in the desired location and so that it will not move while holes are drilled for the screws. This system and process are described in more detail below with reference to the figures.

FIG. 1 is a side view of distraction pins attached to vertebrae in accordance with an illustrative embodiment. Specifically, a distraction pin 125 is attached to a vertebra 100 and a distraction pin 130 is attached to a vertebra 110. The distraction pins span an intervertebral disc 115 between the vertebra 100 and a vertebra 105, and an intervertebral disc 120 between the vertebra 105 and the vertebra 110. As illustrated in FIG. 1, the distraction pins 125 and 130 each include a threaded end which is threaded into the vertebra to hold it securely in place. In an illustrative embodiment, the distraction pins 125 and 130 are positioned along the midline of the spine when viewed from the front (i.e., anterior).

Figure 2:
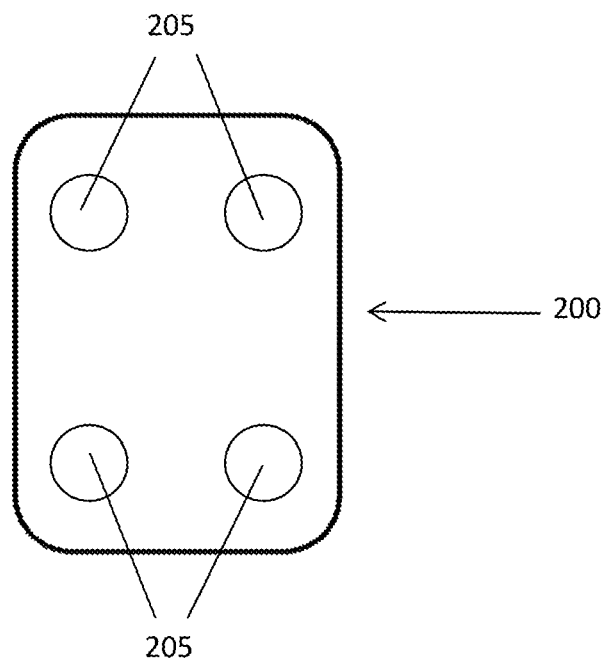
FIG. 2 is a front view, or an anterior view, of a cervical spine plate in accordance with an illustrative embodiment.

FIG. 2 is a front view of a cervical spine plate 200 in accordance with an illustrative embodiment. The cervical spine plate 200 includes a plurality of holes 205 that are configured to receive fasteners such that the cervical spine plate 200 can be secured to the vertebral bodies above and below a fusion. The fusion over which the cervical spine plate 200 spans can be a single level fusion (i.e., a fusion in which a single intervertebral disc is removed and fused) or a multi-level fusion (i.e., a fusion in which a plurality of intervertebral discs are removed and fused). The fasteners used to secure the cervical spine plate 200 are typically screws, although other types of fasteners may be used in alternative embodiments. As illustrated in FIG. 2, a single-level plate includes four holes, two of which are used to secure the cervical spine plate 200 to a vertebra above, or cephalad to, the fusion and two of which are used to secure the cervical spine plate 200 to a vertebra below, or caudal to, the fusion. In alternative embodiments, fewer or additional holes may be used. For example, in a multilevel fusion, the cervical spine plate may include additional sets of holes such that the plate can be secured to one or more vertebra that occur in between the vertebra directly above the fusion and the vertebra directly below the fusion.

FIG. 3A is a front view of a bracket 300 that attaches to the cervical spine plate and the cervical spine plate alignment guide in accordance with an illustrative embodiment. An upper portion 305 of the bracket sits on top of the cervical spine plate, whereas side portions 310 of the bracket wrap around the edges of the cervical spine plate, thus attaching the bracket 300 to the plate. The bracket 300 includes an anteriorly protruding component 315 that accommodates the cervical spine plate alignment guide. The cervical spine plate alignment guide is secured to the bracket 300 via a threaded post 320. In an alternative embodiment, the cervical spine plate alignment guide is secured to the bracket via an alternative locking mechanism.

The bracket 300 is depicted attached to a cervical spine plate 200 in FIG. 3B, in accordance with an illustrative embodiment. The upper portion 305 of the bracket 300 sits on top of (i.e., anterior to) the plate 200, with the side portions 310 of the bracket 300 wrapped around the edges and extending underneath (i.e., posterior to) the cervical spine plate 200. The bracket 300 attaches to the cervical spine plate 200 by an interference fit consisting of the upper portion 305 of the bracket 300 engaging the top of the plate 200 and the side portions 310 of the bracket 300 engaging the sides and bottom of the plate 200. In one embodiment, a back portion of the bracket 300 includes lips, edges, or teeth that are configured to contact a rear side of the cervical spine plate 200 such that the bracket 300 can be secured to the cervical spine plate 200. In one embodiment, the lips, edges, or teeth are small such that they extend along only a small portion of the rear side of the cervical spine plate 200 (i.e., just enough to allow the bracket 300 to secure the cervical spine plate 200). The bracket 300 can be semi-flexible such that the surgeon can bend bracket 300 to open the lips/edges/teeth. The surgeon can then place the bracket 300 on the cervical spine plate 200 and bend the bracket 300 back such that the lips/edges/teeth wrap around to the rear side of the cervical spine plate 200. As discussed in more detail below, the surgeon can then reverse the process to remove the bracket once the cervical spine plate 200 is secured to the patient.

In an alternative embodiment, the bracket 300 can include two halves that are slidably mounted to one another via grooves, slots, male/female connection, etc. In such an embodiment, the surgeon does not have to bend the bracket to attach it and remove it from the cervical spine plate 200. Rather, in such an embodiment, the surgeon can slide the bracket open, place the bracket on the cervical spine plate 200, and slide the bracket closed such that the lips/edge/teeth wrap around at least a portion of the rear side of the cervical spine plate 200. In an alternative embodiment, the bracket 300 could be attached to the plate via a screw or post.

FIG. 3C is a cross-sectional view of the bracket 300 attached to the cervical spine plate 200 in accordance with an illustrative embodiment. The bracket includes a protruding component 315 that accommodates the cervical spine plate alignment guide. The cervical spine plate alignment guide is secured to the bracket via a post 320. Post 320 may or may not be threaded, depending on the embodiment.

Figure 4A:
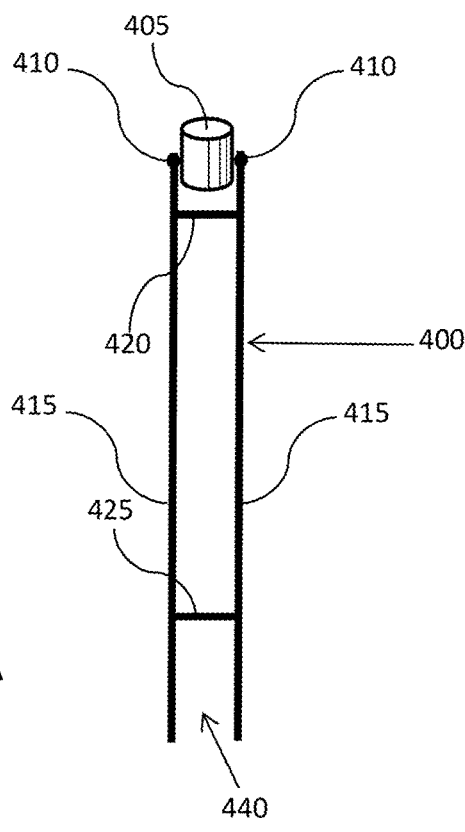
FIGS. 4A, 4B, 4C, and 4D are front views, or anterior views, of 4 different embodiments of the cervical spine plate alignment guide, in accordance with illustrative embodiments.

FIG. 4A is a front view of an alignment guide 400 in accordance with an illustrative embodiment. In the embodiment of FIG. 4, the alignment guide 400 includes an open cylinder or ring 405 that can slide over a distraction pin that is inserted in a vertebra. In alternative embodiments, different configurations and/or shapes may be used for the alignment guide 400. In an illustrative embodiment, the ring 405 has an inner diameter that is slightly larger than the distraction pin such that the ring can be slid over the distraction pin down to the vertebral body such that the alignment guide 400 can be secured to the patient via its intimate connection with the distraction pin. In another illustrative embodiment, the ring 405 is pivotally mounted via pins 410 that run from the outer edges of the ring 405 to bars 415 of the alignment guide 400. In such an embodiment, the ring 405 is able to pivot up to 360°. Alternatively, the ring 405 may be attached to the bars 415 via a semi-rigid material (e.g., rubber) that allows the ring 405 to pivot in an up/down direction (in accordance with the orientation illustrated in FIG. 4A). The bars 415 are connected by cross members 420 and 425 to form a rigid construct having an opening 440 formed by the bars 415 and cross member 425. The opening 440 accommodates a distraction pin that is inserted in a vertebra. Thus the open cylinder 405 slides onto a distraction pin in one vertebra and the opening 440 accommodates a second distraction pin in a different vertebra such that the alignment guide is further secured to the patient. In an alternative embodiment, opening 440 does not need to accommodate a second distraction pin. In the orientation illustrated in FIG. 4A, the ring 405 is positioned to be placed over a distraction pin that is inserted above a fusion and the slot 440 is configured to receive a distraction pin that is inserted below the fusion. In alternative embodiments, the slot 440 can be at the top and the ring 405 may be at the bottom.

Figure 4B:
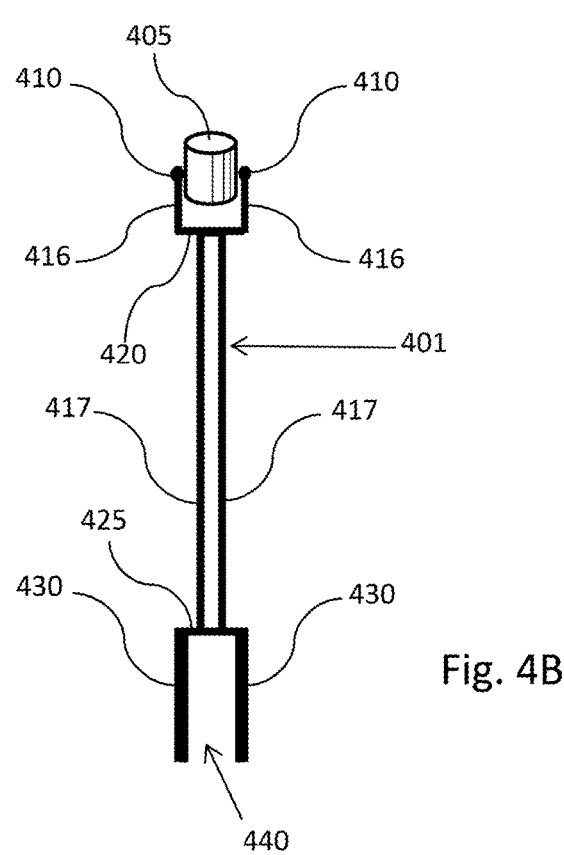

FIG. 4B is a front view of an alternative embodiment of an alignment guide 401 in accordance with an illustrative embodiment. In this embodiment, the pins 410 connect the ring 405 to short bars 416, which are connected by cross member 420. Bars 417 then connect to cross member 425, which connects to bars 430, thus making an opening 440.

Figure 4C:
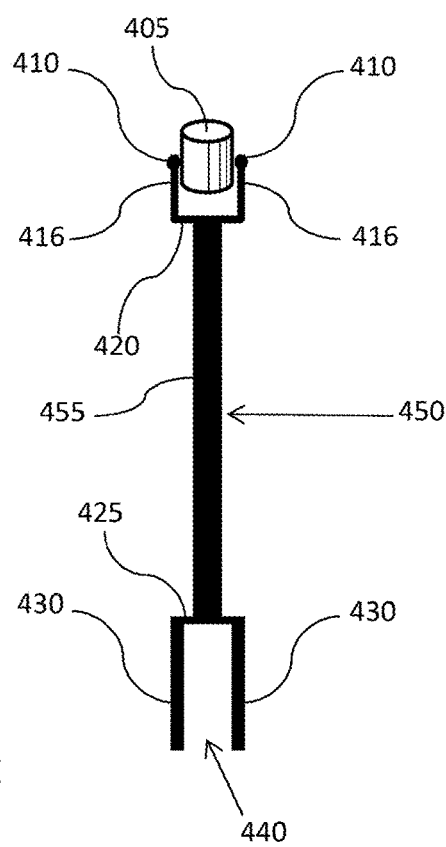

FIG. 4C is a front view of an alternative embodiment of an alignment guide 450 in accordance with an illustrative embodiment. In this embodiment, the pins 410 connect the ring 405 to short bars 416, which are connected by cross member 420. A single bar 455 then connects to cross member 425, which connects to bars 430, thus making an opening 440.

Figure 4D:
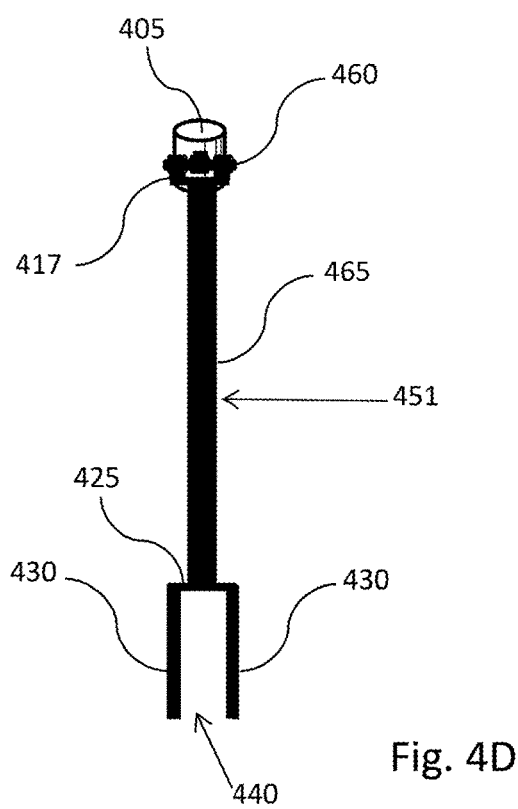

FIG. 4D is a front view of an alternative embodiment of an alignment guide 451 in accordance with an illustrative embodiment. In this embodiment, a hinge 460 connects the ring 405 to cross member 417. Cross member 417 then connects to bar 465. Bar 465 connects to cross member 425, which connects to bars 430, thus making an opening 440. In an alternative embodiment, bar 465 can terminate without connecting to a cross members, thus eliminating opening 400, with the alignment guide attaching to a single distraction pin. In alternative embodiments, ring 405 can be connected by other methods to bars of other configurations to make an opening 440.

FIG. 5A is a front view of a bracket 300 with protruding component 315 between the bars 415 of an alignment guide 400 in accordance with an illustrative embodiment. The bracket 300 includes a protruding component 315 and a post 320, and is attached to a cervical spine plate 200. FIG. 5B shows the configuration in FIG. 5A with the addition of a fastener 525, in accordance with an illustrative embodiment. The fastener 525 can be a nut or other fastener mechanism, depending on the embodiment. Fastener 525 screws onto threaded post 320 and secures an alignment guide 400 to a bracket 300, such that plate 200 is attached to bracket 300 which is attached to alignment guide 400. FIG. 5C is a front view of an alternative embodiment of bracket 300 with protruding component 315 and threaded post 320 replaced by protruding components 555 and 560 that together form a threaded hole that can accept a bolt, in accordance with an illustrative embodiment. The bars of alignment guide 401 run in between components 555 and 560. FIG. 5D shows the configuration in FIG. 5C with a bolt 570 now screwed into the threaded hole formed by components 555 and 560 in accordance with an illustrative embodiment. This secures an alignment guide 401 to bracket 300, such that plate 200 is attached to bracket 300 which is attached to alignment guide 401.

Figure 6A:
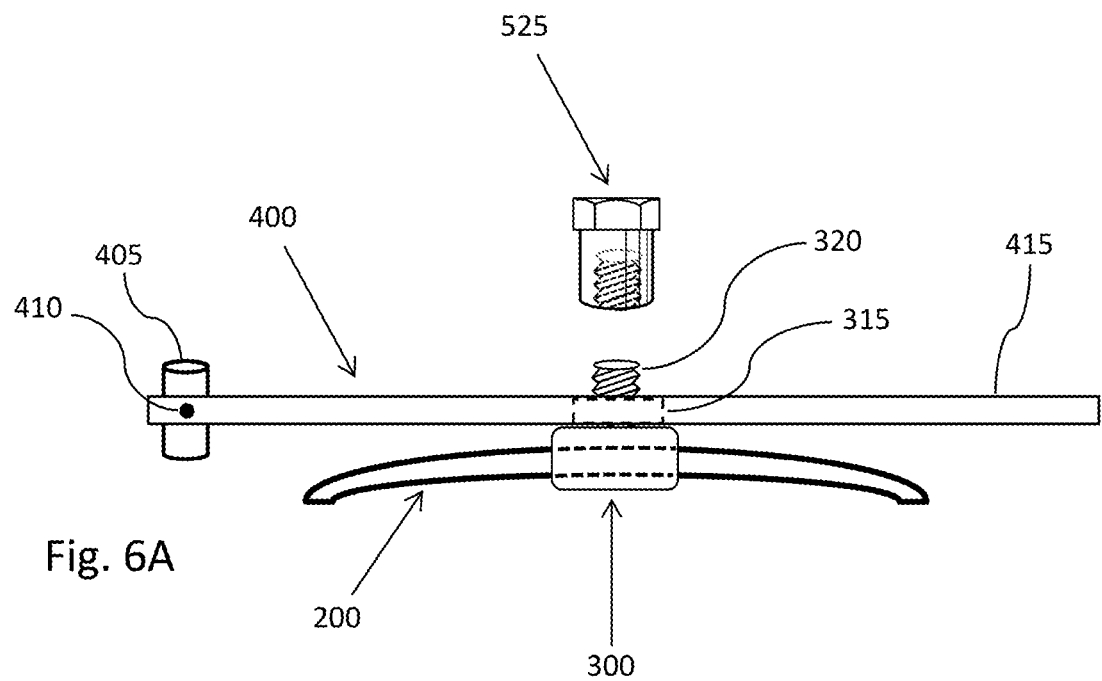
FIGS. 6A and 6B are side views of 2 different embodiments a cervical spine plate alignment guide being attached to a cervical spine plate via a bracket, in accordance with illustrative embodiments.
Figure 6B:
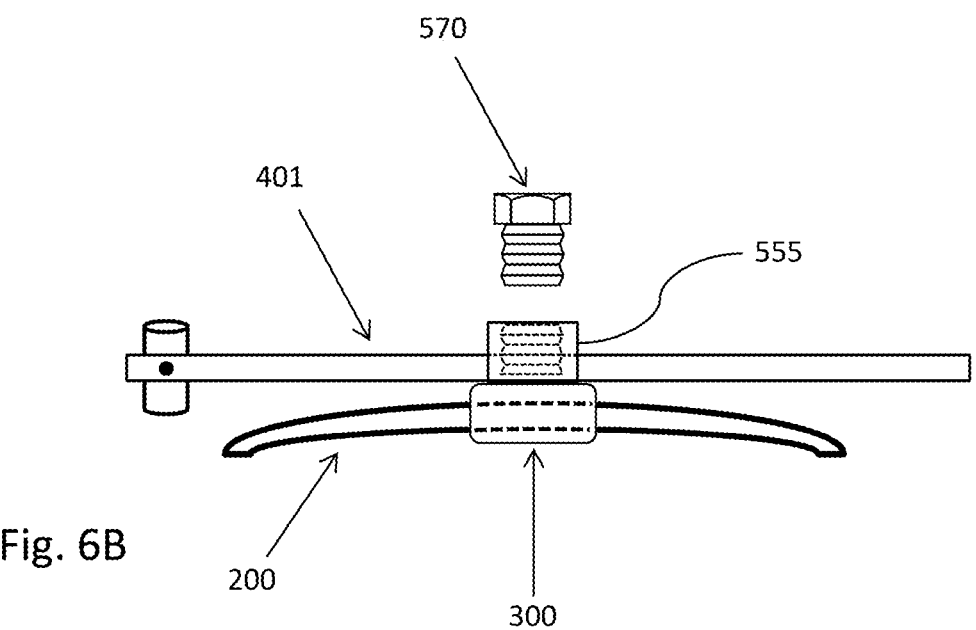

FIG. 6A is a side view of cervical spine plate 200 with an attached bracket 300 and an alignment guide 400 in accordance with an illustrative embodiment. Ring 405 is attached to the alignment guide 400 via pins 410, allowing the ring 405 to pivot. The bracket 300 includes a protruding component 315 that accommodates the cervical spine plate alignment guide. The cervical spine plate alignment guide is secured to the bracket via a threaded or unthreaded post 320 and a nut or fastener 525. Here the nut 525 is depicted in an unsecured fashion, ready to be threaded onto post 320, thus securing the plate 200 to the alignment guide 400 via bracket 300. FIG. 6B is an alternative embodiment of an alignment guide 401, in accordance with an illustrative embodiment. Threaded post 320 depicted in FIG. 6A is replaced by protruding components 555 and 560 (560 not pictured in FIG. 6B because it is a side view, but 560 is pictured in FIG. 5C) that together form threads that can accept a bolt 570, and the bars of alignment guide 401 run in between components 555 and 560. Here the bolt 570 is depicted in an unsecured fashion, ready to be threaded into the threads formed by protruding components 555 and 560, thus securing the plate 200 to the alignment guide 401 via bracket 300.

FIG. 7A is a side view of a cervical spine plate 200 positioned on vertebrae in accordance with an illustrative embodiment. In FIG. 7A, representing a 2-level anterior cervical spine fusion, the intervertebral discs 115 and 120 illustrated in FIG. 1 have been surgically removed and replaced with cages (or bone grafts) 725 and 730. In order to stabilize the spine to facilitate the fusion, the surgeon then secures the cervical spine plate 200 to the vertebra 100 above (i.e., cephalad to) the fusion sites and the vertebra 110 below (i.e., caudal to) the fusion sites. As discussed above, the surgeon attaches cervical spine plate 200 to an alignment guide 401 and secures the alignment guide 401 to the patient. As illustrated in FIG. 7A, a ring 405 of an alignment guide 401 is placed over the distraction pin 125, and a slot 440 of the alignment guide 401 is placed over the distraction pin 130 such that the alignment guide 401 is rigidly secured to the patient with respect to the cephalad-caudal and medial-lateral directions. In an alternative embodiment, pins other than distraction pins may be used to secure the alignment guide 401 to vertebrae, and such pins may be threaded or unthreaded. As discussed above, the distraction pins 125 and 130 (or other pins) are placed along a midline of the cervical spine, thus ensuring the plate will also be placed in the midline of the cervical spine.

FIG. 7B shows the alignment guide 401 further secured to distraction pins 125 and 130 with locking rings 750 that slide onto the distraction pins and then the locking mechanism 751 is engaged, thus holding the back portion of the cervical plate 200 flush with the anterior vertebral bodies, in accordance with an illustrative embodiment. Locking rings 750 secure the plate and alignment guide in the anterior-posterior plane. Once the plate is positioned in the desired cephalad-caudal position, and the plate is flush with the vertebral bodies and locking mechanisms 751 engaged, the bolt or fastener 570 is tightened, thus rigidly securing the cervical spine plate into position on the cervical spine. FIG. 7A shows bolt or fastener 570 in its untightened configuration, whereas FIG. 7B shows the bolt or fastener 570 in its tightened position. Once the alignment guide 401 (which is attached to the cervical spine plate 200 via bracket 300) is secured to the patient, the surgeon can adjust the plate if necessary by loosening the fastener 570, moving the plate cephalad or caudal, and retightening the fastener 570. As such, the surgeon can be confident that the cervical spine plate 200 is in the proper position. This position is in the midline of the cervical spine based on the relationship of the alignment guide to the distraction pins that are placed in the midline. This position is straight when viewed from the front based on the relationship of the alignment guide bar(s) to the bracket protuberance(s), which is designed with minimal tolerance to prevent any angulation in the medial or lateral direction. This position is in the desired cephalad-caudal position based on the ability to slide the plate only in a cephalad or caudal manner based on the relationship of the alignment guide to the corresponding protruberance(s) on the bracket, and then securing the plate to the alignment guide in a reversible manner. Once the cervical spine plate 200 is properly positioned and secured to the patient via the bracket 300 and its attachment to alignment guide 401, the surgeon then drills holes into the vertebrae using the holes 205 (depicted in FIG. 2) of the cervical spine plate 200 as a guide. The cervical spine plate 200 is then fastened to the vertebral bodies 100 and 110 via threaded screws or fasteners 700 and 705, respectively, that pass through holes 205. The heads of screws or fasteners 700 do not pass through holes 205, instead engaging the plate 200 and serving to compress and hold the plate to the vertebral bodies. In an alternative embodiment, self-drilling screws or fasteners can be used which may eliminate the need to drill into the vertebral bodies. In another alternative embodiment, pins other than distraction pins may be used to secure the alignment guide 401 to vertebrae, and such pins may be threaded or unthreaded. As discussed above, the distraction pins 125 and 130 (or other pins) are placed along a midline of the cervical spine. Once the cervical spine plate 200 is fastened to the vertebral bodies with screws or fasteners 700 and 705, the surgeon can then remove the alignment guide by disengaging locking mechanisms 751, sliding locking rings 750 off the distraction pins 125 and 130, removing bolt or fastener 570, and then disengaging bracket 300 from plate 200. The distraction pins 125 and 130 are then removed, and the surgical procedure completed in a manner well known to those practiced in the art.

Figure 8:
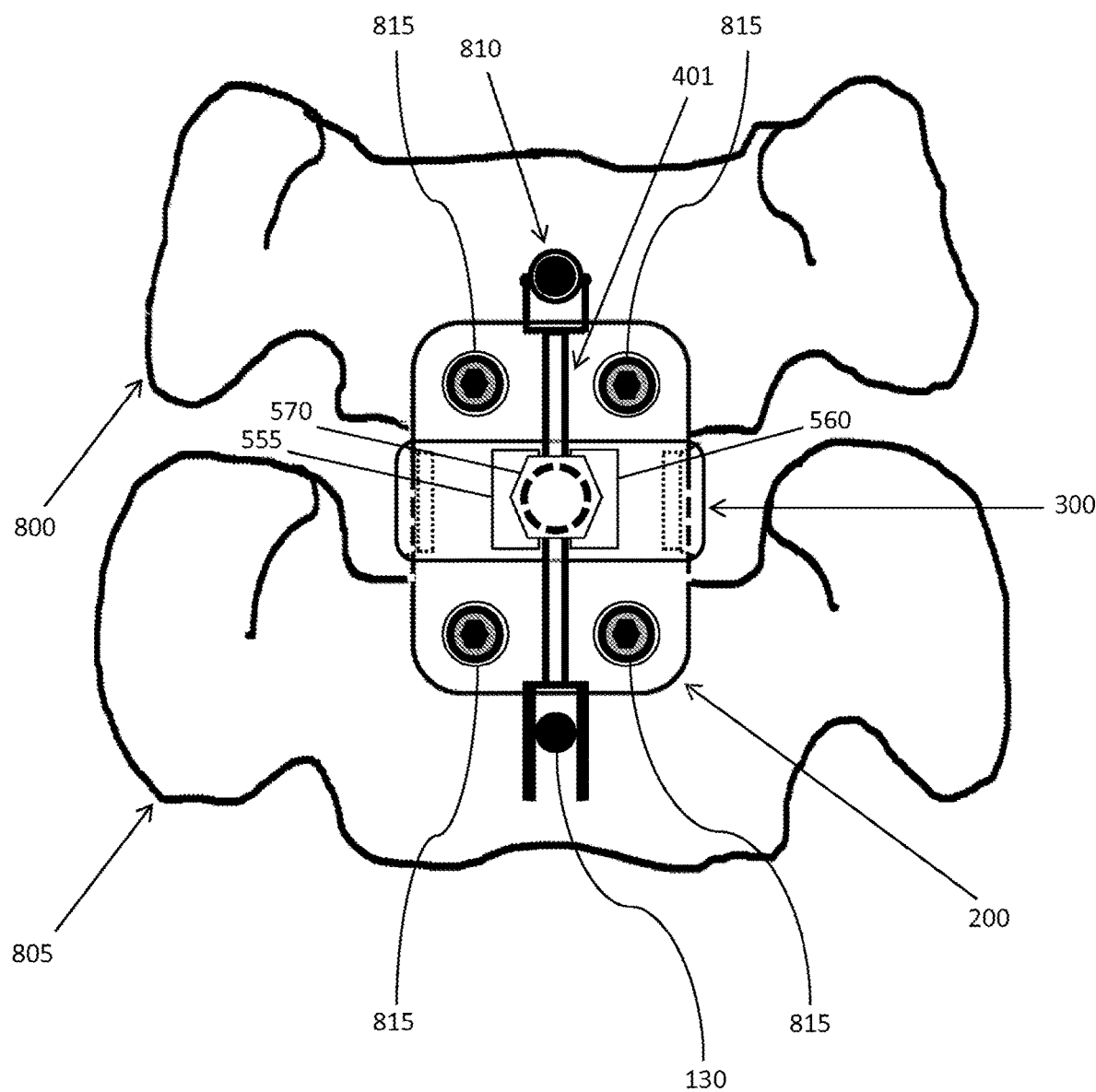
FIG. 8 is a front view, or anterior view, of a single-level anterior cervical spine fusion, with a cervical spine plate attached to an alignment guide, in accordance with an illustrative embodiment.

FIG. 8 is a front view of a single-level cervical spine fusion with an alignment guide 401 attached to a cervical spine plate 200 via a bracket 300, with the cervical spine plate fastened to vertebral bodies 800 and 805, in accordance with an illustrative embodiment. The alignment guide 401 includes a ring (405 in FIGS. 7A and 7B) that has been slid over a distraction pin (125 in FIGS. 7A and 7B), and together the ring and distraction pin are shown as 810 in FIG. 8. The cervical spine plate is fastened to the vertebral bodies by screws or fasteners (700 and 705 in FIG. 7B) that have been placed through holes in the cervical spine plate (205 in FIG. 2), and together the holes in the cervical spine plate along with the screws or fasteners placed through the holes are shown as 815 in FIG. 8. FIG. 8 shows that the distraction pins have been placed in the midline of the cervical spine, the alignment guide is secured to the patient by attaching to or sliding around the distraction pins and thus is also placed in the midline, and by virtue of the cervical spine plate being attached to the alignment guide, the cervical spine plate is placed straight and in the midline of the cervical spine.

Figure 9:
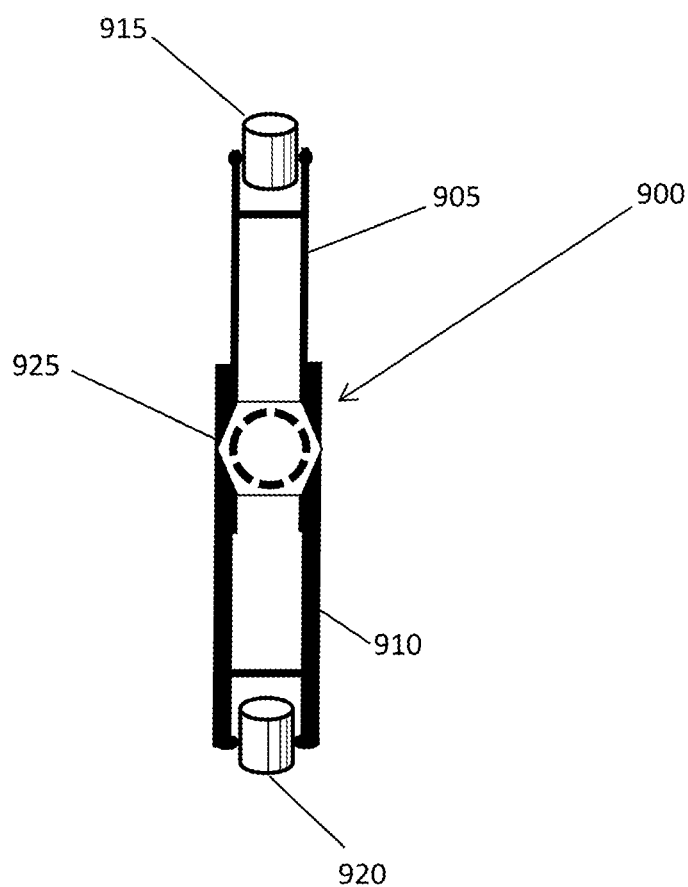
FIG. 9 is a front view, or anterior view, of an alternative embodiment of the cervical spine plate alignment guide, in accordance with an illustrative embodiment.

FIG. 9 is a front view of an alignment guide 900 in accordance with an illustrative embodiment. The alignment guide 900 is an alternative embodiment of an alignment guide 400 as depicted in FIG. 4A and includes an upper ring 915 and a lower ring 920, each of which is configured to slide over distraction (or other) pins that are secured to vertebrae of a patient. In an illustrative embodiment, each of the upper ring 915 and the lower ring 920 is able to articulate, as discussed above with reference to the ring 405 of FIG. 4A. The sidewalls of the alignment guide 900 are formed by upper sidewalls 905 that slidably mate with lower sidewalls 910. The upper sidewalls 905 and lower sidewalls 910 can engage one another via a tongue and groove configuration, a hole and shaft configuration, etc. As a result, the alignment guide 900 is adjustable and can be adjusted to fit different patient anatomies and distraction pins that are different distances apart. A fastener 925 is used to secure the alignment guide 900 to a cervical spine plate as discussed herein.

In an alternative embodiment, a cervical spine plate can be designed with grooves on its front (i.e., anterior) surface in which an alignment guide sits and is confined such that it can slide in only cephalad and caudal directions. Such a cervical spine plate can be designed to include a threaded hole that can accommodate a bolt or fastener that directly secures the alignment guide to the plate once the plate is in the desired position on the cervical spine, thus eliminating the need for a bracket. FIG. 10A is a front view of such a plate, in accordance with an illustrative embodiment. The cervical spine plate 1000 includes a plurality of holes 1005 that are configured to receive fasteners (usually screws) such that the cervical spine plate 1000 can be secured to the vertebral bodies above and below a fusion, analogous to the cervical spine plate and holes as depicted in FIG. 2. Cervical spine plate 1000 has a central groove 1020 in the top or anterior part of the plate, with side walls 1010 that accommodate a cervical spine alignment guide and contain it in such a fashion that the cervical spine plate can slide only cephalad or caudal with respect to the alignment guide. The side walls 415 of cervical alignment guide 400 sit within the groove 1020 (shown in FIG. 10C), contained by side walls 1010 of the cervical spine plate. A central hole 1030 is used to accommodate a fastener to secure the plate to the alignment guide once properly positioned.

FIG. 10B is a cross-sectional view of cervical spine plate 1000, with the cross-section occurring through plane 1040 as shown in FIG. 10A, in accordance with an illustrative embodiment. Groove 1020 is shown along with central hole 1030. FIG. 10C is a front view of cervical spine plate 1000 with alignment guide 400 secured in position in the groove in the cervical spine plate by fastener or bolt 1025, in accordance with an illustrative embodiment. FIG. 10D is a cross sectional view of cervical spine plate 1000 with alignment guide 400 sitting in groove 1020, in accordance with an illustrative embodiment. The cross-section is made through plane 1040 as shown in FIG. 10C. In this cross-sectional figure, the side walls 415 of alignment guide 400 are seen to sit within groove 1020, such that alignment guide 400 is contained within the groove and can slide only in cephalad and caudal directions as discussed herein. Fastener or bolt 1025 is ready to be advanced into hole 1030 to secure the alignment guide 400 to the plate 1000 once the plate is positioned in the desired location.

FIG. 10E is a cross sectional view of a cervical spine plate 1050 in accordance with an illustrative embodiment. The cross-section is made through plane 1040 as shown in FIG. 10C. Cervical spine plate 1050 is an alternative embodiment of a cervical spine plate that directly attaches to an alignment guide, with a channel 1055 created by protuberances 1060 that project from the front or anterior portion of the plate. Thus the channel 1055 is created with protuberances from the plate rather than a groove in the plate such as groove 1020 in FIG. 10A. The channel 1055 serves the same function as groove 1020, that is, containing the cervical spine plate alignment guide side walls such that the alignment guide can slide only in cephalad or caudal directions. In an alternative embodiment, a cervical spine plate can be made with a combination of a groove and protuberances to contain the side walls of the cervical spine alignment guide. In another alternative embodiment, the groove or channel can be made variably wider than the width of the alignment guide, to allow adjustment in medial and lateral directions in addition to cephalad and caudal directions.

Figure 11:
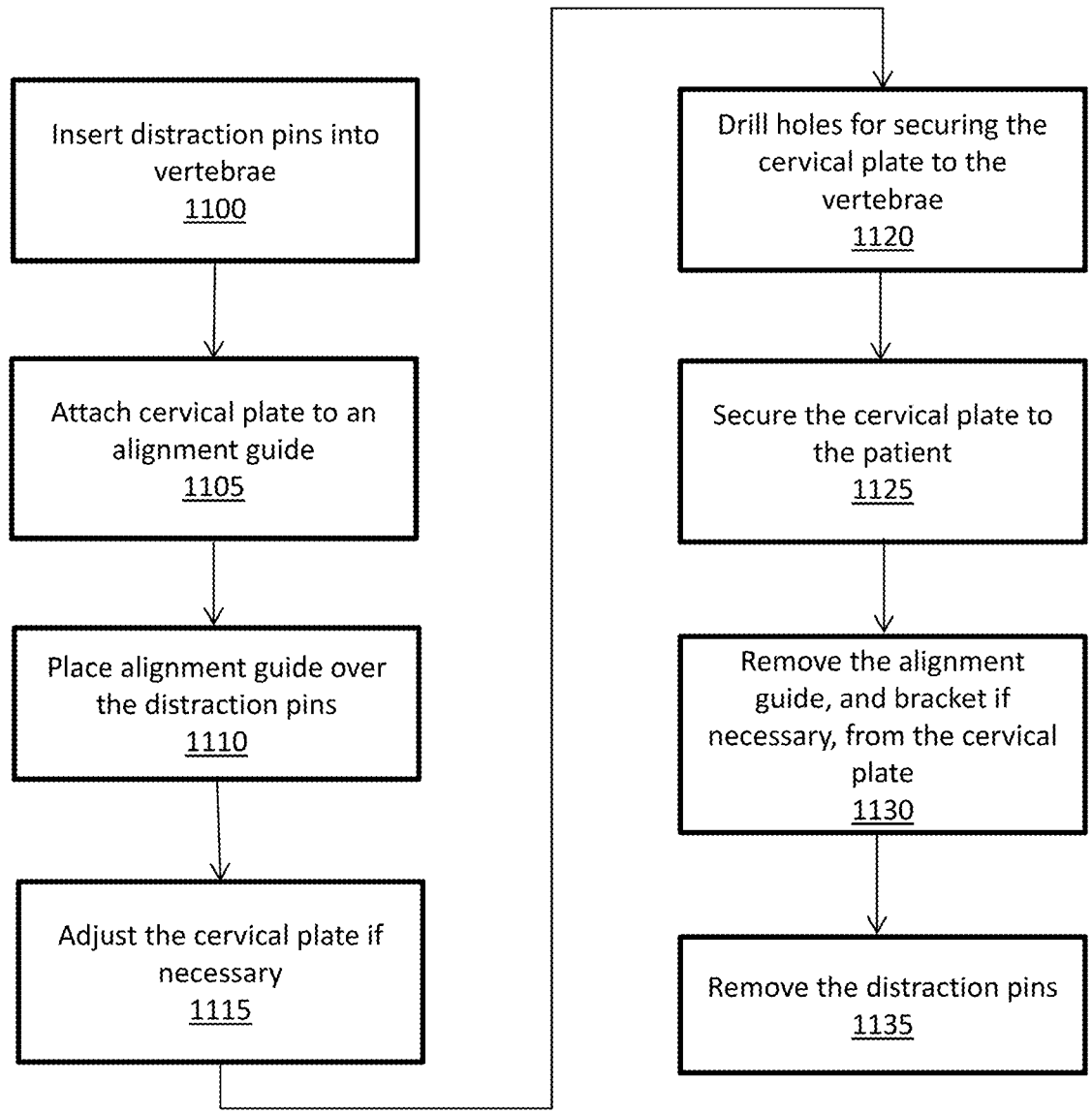
FIG. 11 is a flow diagram depicting a process for mounting a cervical spine plate using an alignment guide in accordance with an illustrative embodiment.

FIG. 11 is a flow diagram depicting a process for mounting a cervical spine plate using an alignment guide in accordance with an illustrative embodiment. In alternative embodiments, fewer, additional, and/or different operations may be performed. Additionally, the use of a flow diagram is not meant to be limiting with respect to the order of operations performed. After preliminary surgical procedures are performed, a surgeon inserts distraction pins into vertebrae in an operation 1100. In an illustrative embodiment, the distraction pins are inserted into the midline of the patient's spine. As known to those of skill in the art, the surgeon can use the distraction pins to help remove one or more intervertebral discs and replace them with bone grafts or cages. In an embodiment in which distraction pins are not required, the surgeon can use other types of pins.

In an operation 1105, the surgeon attaches a cervical spine plate to an alignment guide. In an illustrative embodiment, the cervical spine plate is attached to the alignment guide as discussed above with reference to FIGS. 5B and 5D, and FIG. 10C. In an operation 1110, the surgeon places the alignment guide over the distraction pins. Specifically, the surgeon slides the rings/slots of the alignment guide over the distraction pins such that the alignment guide, and therefore the cervical spine plate, are rigidly secured to the patient. In an operation 1115, the surgeon adjusts the cervical spine plate if necessary. Such adjustment can be performed by loosening the fastener that secures the alignment guide to the cervical spine plate, adjusting the cervical spine plate to the desired orientation, and then re-tightening the fastener to secure the cervical spine plate in the desired orientation.

In an operation 1120, the surgeon drills holes for securing the cervical spine plate to the vertebra. In an illustrative embodiment, the holes in the cervical spine plate act as a guide for the drilling. In an operation 1125, the surgeon secures the cervical spine plate to the patient by inserting fasteners through the cervical spine plate and into the drilled holes. In an illustrative embodiment, the fasteners are screws. In an operation 1130, the surgeon removes the alignment guide, and removes the bracket if a bracket was used, from the cervical spine plate. Specifically, the surgeon can loosen the fastener on the alignment guide, remove the alignment guide by sliding it back off of the distraction pins, and manipulate the bracket such that it can be removed from the cervical spine plate. In an operation 1135, the surgeon removes the distraction pins from the patient. The surgeon can then complete the surgical procedure as known to those of skill in the art.

The alignment guides described herein can be made in a variety of lengths to accommodate single-level and multi-level fusions, and suitable to various patient anatomies. The alignment guide and other components can be made from stainless steel, titanium, titanium-alloy, cobalt-chrome, or any suitable material that is determined to withstand the biomechanical stresses under which they will be placed.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A cervical spine plate attachment system comprising:
  a cervical spine plate that includes:
    a first surface configured to rest upon a first vertebra and a second vertebra;
    a second surface opposite the first surface and facing away from the first vertebra and the second vertebra; and
    a plurality of holes each configured to receive a fastener, wherein the plurality of holes include a first upper hole and a second upper hole to secure the cervical spine plate to the first vertebra and a first lower hole and a second lower hole to secure the cervical spine plate to the second vertebra;

an alignment guide that detachably mounts to the cervical spine plate, wherein the alignment guide comprises a pair of bars that rest upon the second surface of the cervical spine plate when the alignment guide is mounted to the cervical spine plate, wherein the pair of bars rest upon a portion of the second surface of the cervical spine plate that is positioned between the first upper hole and the second upper hole and between the first lower hole and the second lower hole; and an alignment guide fastener configured to secure the alignment guide to the cervical spine plate.

2. The cervical spine plate attachment system of claim 1, wherein the cervical spine plate includes a threaded hole that is configured to receive the alignment guide fastener, and wherein the threaded hole is positioned between the pair of bars of the alignment guide when the alignment guide is mounted to the cervical spine plate.

3. The cervical spine plate attachment system of claim 2, wherein the threaded hole is positioned in a center of the cervical spine plate.

4. The cervical spine plate attachment system of claim 1, wherein the alignment guide includes a first connector proximate to a first end of the alignment guide and configured to attach to a first pin inserted into the first vertebra.

5. The cervical spine plate attachment system of claim 4, wherein the alignment guide includes a second connector proximate to a second end of the alignment guide and configured to attach to a second pin inserted into the second vertebra.

6. The cervical spine plate attachment system of claim 5, further comprising a first locking ring configured to slide over the first pin to secure the first connector of the alignment guide to the first pin and a second locking ring configured to slide over the second pin to secure the second connector of the alignment guide to the second pin.

7. The cervical spine plate attachment system of claim 5, wherein the first connector comprises a ring that pivots.

8. The cervical spine plate attachment system of claim 7, wherein the second connector comprises a ring.

9. The cervical spine plate attachment system of claim 7, wherein the second connector of the alignment guide comprises an extension of the pair of bars that form the alignment guide.

10. The cervical spine plate attachment system of claim 1, wherein the second surface of the cervical spine plate includes protuberances that form a channel, and wherein the channel is configured to receive the pair of bars of the alignment guide.

11. The cervical spine plate attachment system of claim 10, wherein the cervical spine plate includes a threaded hole that is configured to receive the alignment guide fastener, and wherein the threaded hole is positioned in the channel formed by the protuberances.

12. The cervical spine plate attachment system of claim 1, further comprising one or more cross members mounted between the pair of bars of the alignment guide and configured to maintain the pair of bars parallel to one another.

13. The cervical spine plate attachment system of claim 1, wherein the alignment guide fastener includes a head and a threaded portion, and wherein the head is configured to contact the pair of bars of the alignment guide to secure the alignment guide to the cervical spine plate.

14. A method for mounting a cervical spine plate, the method comprising:

mounting an alignment guide to a cervical spine plate that includes a first surface configured to rest upon a first vertebra and a second vertebra and a second surface opposite the first surface, wherein the alignment guide is mounted such that at least a portion of the alignment guide rests upon the second surface of the cervical spine plate;

attaching a first connector of the alignment guide to a first distraction pin that is mounted to a first vertebra;

attaching a second connector of the alignment guide to a second distraction pin that is mounted to a second vertebra;

using openings in the cervical spine plate as a guide, drilling holes into the first vertebra and the second vertebra; and securing the cervical spine plate to the first vertebra and the second vertebra by placing fasteners through the openings in the cervical spine plate and into the drilled holes.

15. The method of claim 14, further comprising removing the alignment guide from the cervical spine plate.

16. The method of claim 14, further comprising mounting the first distraction pin at a midline of the first vertebra and mounting the second distraction pin at a midline of the second vertebra.

17. The method of claim 14, further comprising securing the alignment guide to the first and second distraction pins by placing a first locking ring over an end of the first distraction pin and placing a second locking ring over an end of the second distraction pin.

18. The method of claim 14, wherein mounting the alignment guide to the cervical spine plate includes positioning the alignment guide in a channel formed by protuberances on the second surface of the cervical spine plate.

* * * * *